United States Patent
Ygartua

(10) Patent No.: US 8,548,748 B2
(45) Date of Patent: Oct. 1, 2013

(54) DETERMINING THIN FILM STACK FUNCTIONAL RELATIONSHIPS FOR MEASUREMENT OF CHEMICAL COMPOSITION

(75) Inventor: Carlos L. Ygartua, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 305 days.

(21) Appl. No.: 13/195,063

(22) Filed: Aug. 1, 2011

(65) Prior Publication Data

US 2013/0035872 A1 Feb. 7, 2013

(51) Int. Cl.
*G01N 31/00* (2006.01)

(52) U.S. Cl.
USPC .................................................. 702/28

(58) Field of Classification Search
USPC .................................................. 702/28
See application file for complete search history.

(56) References Cited

U.S. PATENT DOCUMENTS

| 4,707,611 | A | 11/1987 | Southwell |
| 2004/0027580 | A1 | 2/2004 | Bosser et al. |
| 2009/0319196 | A1* | 12/2009 | Schaller et al. ............... 702/31 |

FOREIGN PATENT DOCUMENTS

| RU | 2406078 | 1/2010 |
| WO | 8908856 | 9/1989 |

* cited by examiner

*Primary Examiner* — Aditya Bhat
(74) *Attorney, Agent, or Firm* — Luedeka Neely Group, P.C.; Rick Barnes

(57) ABSTRACT

A method for determining chemical composition from optical properties of a stack formed with a process, by preparing test samples of the stack using known and intentional variations to the process to affect a variation in the chemical composition, measuring the optical properties of the test samples, measuring the chemical composition of the test samples, performing a processor-based regression analysis to determine an optical state function including correlations between the optical properties of the test samples and the chemical composition of the test samples, fabricating production samples of the stack using the process, measuring the optical properties of the production samples, and estimating the chemical composition of the production samples using the optical state function.

4 Claims, 1 Drawing Sheet

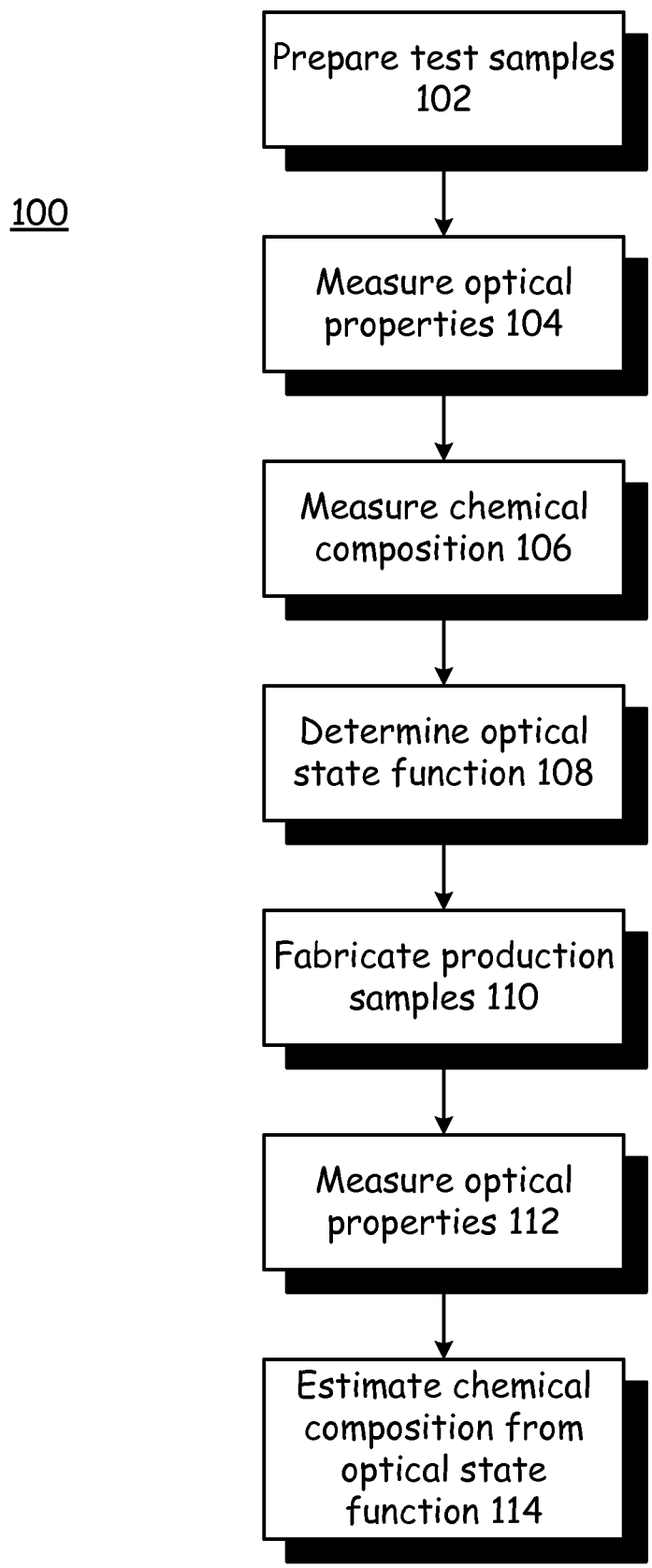

DETERMINING THIN FILM STACK FUNCTIONAL RELATIONSHIPS FOR MEASUREMENT OF CHEMICAL COMPOSITION

FIELD

This invention relates to the field of integrated circuits. More particularly, this invention relates to using the optical properties of thin film stacks to estimate the chemical composition of thin film stacks.

INTRODUCTION

In very general terms, integrated circuits are fabricated by forming a thin film layer of a given material on a substrate, patterning or otherwise processing the layer, and then repeating that cycle for a number of additional layers and different materials. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

The physical properties of these layers, such as thickness, chemical composition, etc., is of extreme importance, as they determine the electrical properties of the integrated circuit fabricated therefrom. However, the chemical composition of these layers is often relatively difficult to determine, especially on production integrated circuits, and more especially in a non-destructive and relatively speedy manner.

What is needed, therefore, is a system that reduces problems such as those described above, at least in part.

SUMMARY OF THE CLAIMS

The above and other needs are met by a method for determining chemical composition from optical properties of a stack by preparing an incomplete sample space of test samples of the stack having varied chemical composition, measuring the optical properties of the test samples, measuring the chemical composition of the test samples, performing a processor-based regression analysis to determine an optical state function including correlations between the optical properties of the test samples and the chemical composition of the test samples, fabricating production samples of the stack using the process, measuring the optical properties of the production samples, and estimating the chemical composition of the production samples using the optical state function.

The optical state function provides a more flexible and powerful method for correlating optical properties and chemical composition than other methods previously used, such as effective medium refractive index models (with each component representing a chemical component), refractive index lookup models (where the lookup parameter is a chemical concentration), or direct correlation of refractive index at a particular wavelength with the concentration of one chemical element. The optical state function can use the parameters (or algebraic combinations of the parameters and for example film layer thickness) from previous methods as optical state variables to achieve better correlation than the original method between chemical composition and optical properties.

In this manner, the very complex and often difficult to determine chemical composition of the stack can be estimated using the relatively easily measured optical properties of the stack.

In various embodiments according to this aspect of the present invention, the optical properties are measured using at least one of visible light and ultraviolet light. In some embodiments the optical properties are refractive index as measured at more than one wavelength. In some embodiments the optical properties are refractive index as measured at as many wavelengths as there are elements within the stack.

BRIEF DESCRIPTION OF THE DRAWINGS

Further advantages of the invention are apparent by reference to the detailed description when considered in conjunction with the FIGURE, which is not to scale so as to more clearly show the details, wherein like reference numbers indicate like elements, and which depicts a flow-chart according to an embodiment of the present invention.

DETAILED DESCRIPTION

Various embodiments of the present invention provide a method of determining a functional relationship between optical measurements of a stack and the chemical composition. As defined herein, the term "stack" implies one or more thin film layer disposed on top of one another, either patterned (grating) or unpatterned, and formed of one or more different materials. A functional relationship (called the optical state function herein) is used in conjunction with an optical measurement to determine one or more of the concentrations of chemical constituents (chemical composition) of layers within the film stack. One application is stacks with complex chemical properties, where each of the chemical constituents has an influence on the optical characteristics of the stack and the resultant optical stack measurements. The optical measurements can be accomplished using either visible or ultraviolet light, for example.

Overview

With reference now to the FIGURE, there is depicted a flow-chart for a basic overview of a method 100 according to an embodiment of the present invention. The first step as given in block 102 is to prepare test samples of the stack with different stoichiometry, such as different levels of oxygen, nitrogen, or silicon in a layer of HfSiON. However, as it would typically be most impractical to do so, in some embodiments no effort is made to construct a rectilinear sample space in which all levels of one element are varied evenly or completely across all levels of the other elements. Thus, the sample space produced is incomplete, and would not be useful in constructing a lookup table for different stack stoichiometries.

Optical properties of the test samples are measured, as given in block 104. In one embodiment, the optical properties are the refractive index of the stack. In some embodiments the refractive index is measured at two different wavelengths, and in some embodiments the refractive index is measured at as many different wavelengths as there are different elements in the film stack. These measured optical properties, such as the refractive index, are referred to herein as optical state variables.

The chemical compositions of the test samples are also measured, as given in block 106, such as by using x-ray photoelectron spectroscopy. This determines the actual concentration of each element (or each desired element) in the film stack. It is appreciated that it makes no difference in what order these two measurements (XPS and RI) are performed.

Next, a regression analysis is performed to determine a so-called optical state function that includes correlations between the optical properties of the test samples (the optical state variables) and the chemical composition of the test samples, as given in block 108.

Once the optical state function has been determined, it can be used to determine the chemical composition of production samples. Thus, production samples of the stack are fabricated using the process, as given in block 110. The optical properties of the production samples are measured, as given in block 112, and the chemical composition (stoichiometry) of the production samples are estimated using the optical state function, as given in block 114. More specific details in regard to these basic steps are given in the next section.

Details

An optical state variable matrix is formed from the results of the optical measurement of the stack and the independently-measured chemical composition for a specific stack. Typically, these specific stack samples are prepared with varied properties, such that the variations represent the range of the stack process to be measured. For example, the stack could have various chemical concentrations of two elements, $C(1)$ and $C(2)$. The optical state variables are formulated based on their linearity with respect to the stack properties. The optical state variable matrices (optical state functions) are then:

$$C(1)_i = \sum_{j=1}^{n} l_0 + l_j \times OSV_{ji}$$

and $$C(2)_i = \sum_{j=1}^{n} m_0 + m_j \times OSV_{ji},$$

where $C(1)_i$ and $C(2)_i$ are known concentrations (or other properties) for the $i^{th}$ sample, $l_j$ and $m_j$ are constants, and $OSV_{ji}$ are the $j^{th}$ optical state variable from the $i^{th}$ sample. The values of the constants $l_j$ and $m_j$ are found by using a standard $n^{th}$ order linear regression with $C(1)_i$ and $C(2)_i$ as the dependent variables and with $OSV_{ji}$ as the dependent variables for each set of linear equations. Note that the selection of optical state variables for each element doesn't have to be identical. Once the optimum value of the constants $l_j$ and $m_j$ are found (based on sufficient correlation from the $n^{th}$ order regression), the functional relationship (optical state function) between the optical measurements and the stack properties is defined.

In general, the best correlation has been obtained by using optical state variables that are a function of refractive index (at various wavelengths). This is independent of the type of refractive index or the film stack model used.

The inverse of the optical state variable matrix helps explain some of the motivation for this method. The optical state variables are selected based on their linearity with respect to all of the stack properties. Using the same example described above, the equation for the optical state variables is:

$$OSV_{ki} = \sum_{j=1}^{2} \chi_{k0} + \chi_{kj} \times C(J)_i.$$

Each optical state variable is a linear function of the concentrations of the two elements. Since there are two concentrations, equations for a minimum of two optical state variables are needed. For this case we have:

$$OSV_{1i} = \chi_{10} + \chi_{11} \times C(1)_i + \chi_{12} \times C(2)_i \text{ and } OSV_{2i} = \chi_{20} + \chi_{21} \times C(1)_i + \chi_{22} \times C(2)_i.$$

The constants $\chi_{10}, \chi_{11}, \chi_{12}, \chi_{20}, \chi_{21}, \chi_{22}$ can be resolved with an $n^{th}$ order linear regression. Then $C(1)$ and $C(2)$ can be explicitly solved using:

$$C(1) = \frac{\chi_{12}(OSV_2 - \chi_{20}) - \chi_{22}(OSV_1 - \chi_{10})}{\chi_{12}\chi_{21} - \chi_{11}\chi_{22}}$$

and $$C(2) = \frac{\chi_{21}(OSV_1 - \chi_{10}) - \chi_{11}(OSV_2 - \chi_{20})}{\chi_{12}\chi_{21} - \chi_{11}\chi_{22}}.$$

These equations are essentially the same as those found by doing the $n^{th}$ order linear regression on the optical state variable matrices, which is the optical state function relationship between the optical measurements and the stack properties.

Thus, the number of optical state variables is greater than or equal to the number of independent stack properties, in order for the stack properties to be determined by optical measurements.

One method for solving this problem is to use a refractive index model with parameters that represent the different phases of the stack, where each phase has an expected chemical composition that gives rise to the particular stack properties. The Bruggeman Effective Medium Approximation or a multi-dimensional lookup model can be used to this end, but there are many limitations to these approaches. For the case of a two (chemical) element concentration measurement, the refractive index of the phases of the material (associated with each element) have to remain constant as the concentration of each element changes in the film for the Bruggeman Effective Medium Approximation to be accurate (where the volume fractions are linear with the concentrations of each element). Multi-dimensional lookup models can have restrictions on the parameter distributions, such as that the concentration values could be required to form a rectilinear array For both of these models, correlation between refractive index parameters and thickness generally causes parameters to shift from the values that represent the assumed phase of the material. In the case of the multi-dimensional lookup, the parameters representing the phases could have somewhat arbitrary values, such as if the concentrations are adjusted to fit on a rectilinear grid. All of the problems described above can contribute to poor correlation between the stack properties and the refractive index model parameters. In general, the optical state variable matrix method improves the performance of both the Bruggeman Effective Medium Approximation and the lookup models—the Bruggeman Effective Medium Approximation and the lookup parameters can be used in an optical state variable matrix to generate an optical state function relationship with better correlation than the measured Bruggeman Effective Medium Approximation or lookup model parameters.

The optical measurement of the stack consists of measuring the spectra (ellipsometric or reflectance) and fitting a spectroscopic model to the measured spectra. The spectroscopic model includes the thickness of the films in the stack and the refractive index dispersion of the films and the substrate. In addition, the spectroscopic model could include patterned stack structures that comprise a one or two dimensional grating. The parameters to be measured are specified in a measurement recipe. The recipe also controls the manner in which the spectroscopic model parameters are varied to fit the measured spectra, via a regression algorithm. The recipe reports measured parameters (thickness, refractive index, refractive index model parameters, etc.). The recipe can also report the physical properties of the stack via the optical state function. The optical state variable matrix method can be embedded into a recipe that includes (or has access to) the material property reference data, sampling plan, and user-defined optical state variables. This would allow for an automatic correlation between the model and the parameters.

The chemical composition of the stack is measured independently of the optical properties by a variety of means. Techniques such as Auger electron spectroscopy or x-ray photoelectron spectroscopy are typically used.

The thin films structures measured are typically those that are used to form microelectronic devices, or are test pads designed to monitor the films in the devices.

A first optical state function matrix method was developed using 155-800 nm ellipsometric spectra from a planar film stack of hafnium silicon oxynitride (HfSiON) on SiON on a silicon substrate. The HfSiON/SiON is used as a high-k gate dielectric material. Spectra was measured on samples with various concentrations of hafnium and nitrogen in the HfSiON/SiON on silicon substrate stack. The HfSiON thickness was also variable, such that the atomic concentrations of hafnium and nitrogen in relation to the entire stack would span the entire range of processes to be monitored. The hafnium and nitrogen concentrations in the film stack were measured with x-ray photoelectron spectroscopy. The optical state variables are refractive index at various wavelengths, normalized by the ratio of HfSiON and total stack thickness. For the nitrogen optical state function, an offset to take into account the amount of nitrogen in the SiON is included. A two-dimensional lookup was used for the HfSiON refractive index model. The SiON refractive index and thickness is constant.

A second model was also evaluated for the same sample set. The second model treats the two-layer stack as a single layer mixture of HfSiON and SiON. For this model, refractive indexes at various wavelengths are used for optical state variables, without the thickness normalization used in the two-layer model.

In general the method is widely applicable to the measurement of chemical composition of various film stacks that require process control in the microelectronic industry.

Example

An example of the step of constructing the optical state function is provided below, in reference to Table 1.

TABLE 1

Optical state value matrix for nitrogen (N) fraction for a two-layer model of HfSiON over an underlying SiON layer (over silicon substrate).

| N XPS | normalized n(wavelength) | | | | N offset | t/t avg |
|---|---|---|---|---|---|---|
| | n'(160 nm) | n'(180 nm) | n'(320 nm) | n'(633 nm) | | |
| 0.163 | 1.25485 | 1.33102 | 1.31342 | 1.23278 | 0.08995 | 0.96794 |
| 0.148 | 1.19546 | 1.25045 | 1.19247 | 1.12669 | 0.08850 | 0.99683 |
| 0.171 | 1.29870 | 1.37548 | 1.38232 | 1.29659 | 0.08620 | 1.04450 |
| 0.175 | 1.14695 | 1.20320 | 1.20877 | 1.13649 | 0.09732 | 0.83478 |
| 0.171 | 1.09323 | 1.12613 | 1.09763 | 1.03882 | 0.09720 | 0.83675 |
| 0.124 | 1.09480 | 1.18008 | 1.10199 | 1.03350 | 0.10591 | 0.70284 |
| 0.166 | 1.39328 | 1.47674 | 1.47336 | 1.38229 | 0.07794 | 1.23910 |
| 0.151 | 1.32136 | 1.39416 | 1.31686 | 1.24267 | 0.07767 | 1.24606 |
| 0.095 | 1.41147 | 1.53602 | 1.40556 | 1.31600 | 0.08169 | 1.14581 |

The optical state function that is regressed from this optical state data is: Nitrogen fraction=0.010*n'(160 nm)-0.607n'(180 nm)+0.464n' (320 nm)-0.640*N offset+0.058*T/Tavg+0.347

"N XPS"=fraction of nitrogen measured by x-ray photoelectron spectroscopy in the total stack. If the stack has a stoichiometry defined by HfSiON, then the fraction would be 0.25 (because one-quarter of all of the atoms are nitrogen). In general, the stoichiometry is Hf(x)Si(y)O(z)N(w) where x, y, z, and w are fractions. Since the stack is Hf(x)Si(y)O(z)N(w)/Si(a)O(b)N(c) there is also a contribution to nitrogen from the underlying layer, as described by the N offset.

"n"=refractive index at the wavelengths shown (160, 180, 320, 633 nm)*thickness HfSiON layer/total stack thickness. Thickness HfSiON and total stack (HfSiON+SiON) thickness are measured by standard spectroscopic ellipsometry methods.

"N offset"=estimated fractional contribution of nitrogen in the underlying layer of SiON (actually Si(a)O(b)N(c)) to the total stack. The N offset is based on the assumption that N is relatively constant in the underlying layer 1—it is not intentionally varied. It is calculated by 0.2*thickness SiON/thickness total stack. The value (0.2) used is just an estimate for c in the stoichiometric equation Si(a)O(b)N(c).

"t/tavg"=total stack thickness/t average, where t average is the average thickness of all the samples used in the correlation sample set and total stack thickness is for each individual sample.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for determining chemical composition from optical properties of a stack formed with a process, the method comprising the steps of:
    preparing an incomplete sample space of test samples of the stack having varied chemical composition,
    measuring the optical properties of the test samples,
    measuring the chemical composition of the test samples,
    performing a processor-based regression analysis to determine an optical state function including correlations between the optical properties of the test samples and the chemical composition of the test samples,
    fabricating production samples of the stack using the process,
    measuring the optical properties of the production samples, and
    estimating the chemical composition of the production samples using the optical state function.

2. The method of claim 1, wherein the optical properties are measured using at least one of visible light and ultraviolet light.

3. The method of claim 1, wherein the optical properties are refractive index as measured at more than one wavelength.

4. The method of claim 1, wherein the optical properties are refractive index as measured at as many wavelengths as there are elements within the stack.

* * * * *